United States Patent [19]

Kume et al.

[11] Patent Number: 4,804,394

[45] Date of Patent: Feb. 14, 1989

[54] BENZOXAZINES AND USE AS HERBICIDES

[75] Inventors: Toyohiko Kume; Toshio Goto; Atsumi Kamochi; Naoko Yamaguchi; Akihiko Yanagi, all of Tokyo; Hidenori Hayakawa, Kanagawa; Shigeki Yagi; Hiroshi Miyauchi, both of Tokyo, all of Japan

[73] Assignee: Nihon Tokushu Noyaku Seizo K.K., Tokyo, Japan

[21] Appl. No.: 88,921

[22] Filed: Aug. 24, 1987

[30] Foreign Application Priority Data

Sep. 9, 1986 [JP] Japan .................................. 61-210725
Feb. 10, 1987 [JP] Japan .................................. 62-27194

[51] Int. Cl.[4] ..................... A01N 43/84; C07D 487/04
[52] U.S. Cl. .......................................... 71/92; 71/94; 71/95; 544/79; 544/105
[58] Field of Search ...................... 544/105, 79; 71/92, 71/94, 95

[56] References Cited

U.S. PATENT DOCUMENTS

| | | | |
|---|---|---|---|
| 4,619,687 | 10/1986 | Haga et al. | 71/92 |
| 4,640,707 | 2/1987 | Nagano et al. | 71/96 |
| 4,729,784 | 3/1988 | Kume et al. | 71/95 |
| 4,734,124 | 3/1988 | Chang et al. | 71/92 |

FOREIGN PATENT DOCUMENTS

| | | |
|---|---|---|
| 170191 | 2/1986 | European Pat. Off. . |
| 0176101 | 4/1986 | European Pat. Off. . |

Primary Examiner—Richard L. Raymond
Attorney, Agent, or Firm—Sprung Horn Kramer & Woods

[57] ABSTRACT

Novel benzoxazines of the formula (I)

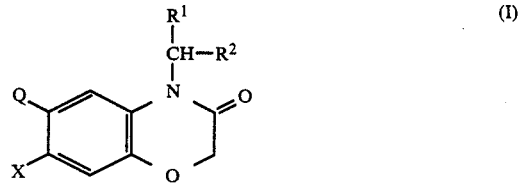

wherein
X is hydrogen or halogen,
$R^1$ is hydrogen or $C_1-C_2$-alkyl,
$R^2$ is cyano, trimethylsilyl, trimethylsilylmethoxycarbonyl, $C_1-C_4$-alkylthio or cyclopropyl and
Q is

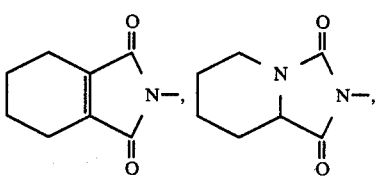

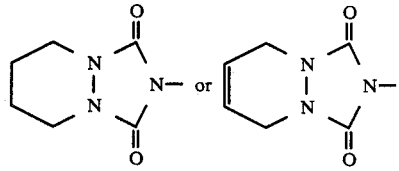

and the use of the novel compounds as herbicides, and intermediates for the preparation of the novel benzoxazines.

10 Claims, No Drawings

BENZOXAZINES AND USE AS HERBICIDES

The present invention relates to novel benzoxazines, to processes for their preparation and to their use as herbicides.

It has already been disclosed that certain tetrahydrophthalimides have herbicidal activities. (see Japanese Patent Laid-Open No. 30,586/1986).

There have now been found novel benzoxazines of the formula (I)

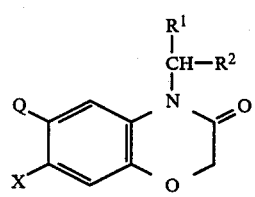
(I)

wherein X is hydrogen or halogen, $R^1$ is hydrogen or $C_1$-$C_2$ alkyl, $R^2$ is cyano, trimethylsilyl, trimethylsilylmethoxycarbonyl, $C_1$-$C_4$ alkylthio or cyclopropyl, and Q is

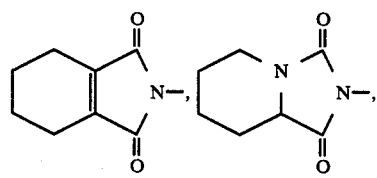

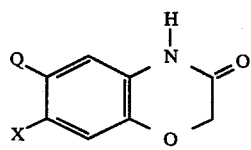  or  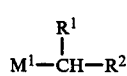,

The compounds of the formula (I) are obtained by a process in which, (a) compounds of the formula (II)

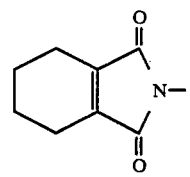
(II)

wherein X and Q have the same meanings as stated above, are reacted with compounds of the formula (III)

$$M^1-\overset{R^1}{\underset{|}{CH}}-R^2$$
(III)

wherein $F^1$ and $R^2$ have the same meanings as stated above, and $M^1$ is halogen, in the presence of an inert solvent, if appropriate, in the presence of a base, or (b) in the case where Q is

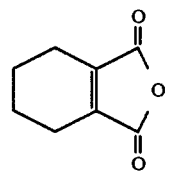

compounds of the formula (IV)

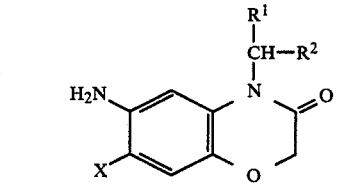
(IV)

wherein X, $R^1$ and $R^2$ have the same meanings as stated above, are reacted with tetrahydrophthalic anhydride of the formula

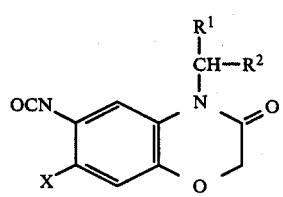

in the presence of acetic acid, or (c) in the case where Q is

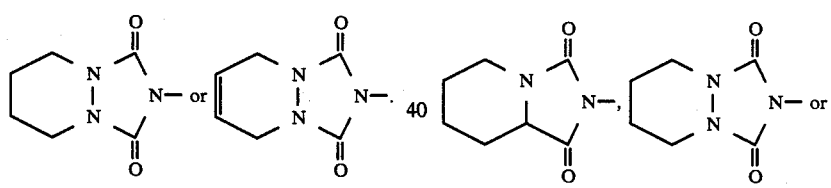

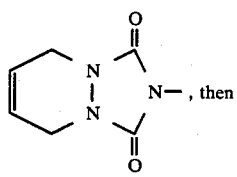, then compounds of the formula (V)

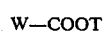
(V)

wherein, X, $R^1$ and $R^2$ have the same meanings as stated above, are reacted with compounds of the formula (IV)

W—COOT (VI)

wherein W is

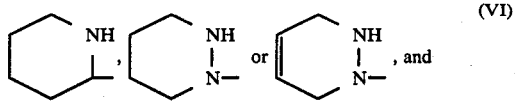 (VI)

T is hydrogen or alkyl, in the presence of an inert solvent, and then said products are cyclized in the presence of an acid or a base.

The novel benzoxazines exhibit powerful herbicidal properties.

Surprisingly, the benzoxazines according to the invention exhibit not only a substantially greater herbicidal action than those known from the prior art, but also a favorable compatibility with crops, namely low phytotoxicity.

Among the benzoxazines according to the invention of the formula (I), preferred compounds are those in which X is hydrogen, fluorine or chlorine,
$R^1$ is hydrogen or methyl,
$R^2$ is cyano, trimethylsilyl, trimethylsilylmethoxycarbonyl, methylthio or cyclopropyl, and

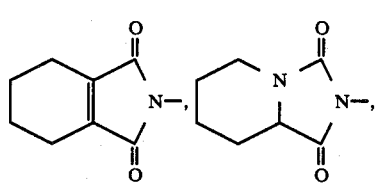

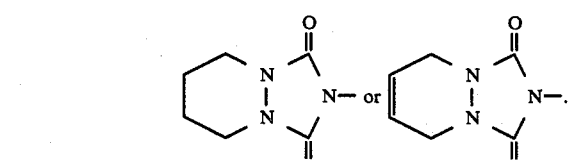

Very particularly preferred benzoxazines of the formula (I) are those in which

X is hydrogen or fluorine,
$R^1$ is hydrogen or methyl,
$R^2$ is cyano, and
Q is

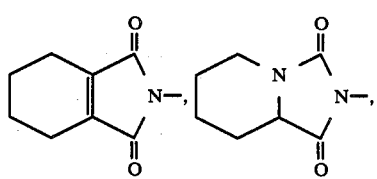

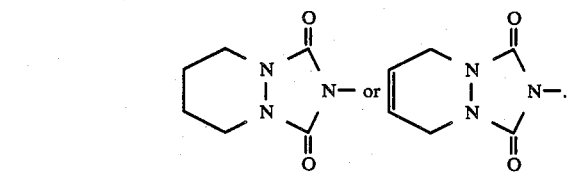

Specifically, the following compounds may be mentioned:

2-[4-cyanomethyl-7-fluoro-2H-1,4-benzoxazin-3(4H)-on-6-yl]-4,5,6,7-tetrahydro-2H-isoindole-1,3-dione, 2-[4-(1-cyanoethyl)-7-fluoro-2H-1,4-benzoxazin-3(4H)-on-6-yl]-4,5,6,7-tetrahydro-2H-isoindole-1,3-dione, 3-[4-cyanomethyl-7-fluoro-2H-1,4-benzoxazin-3(4H)-on-6-yl]-1,5-tetramethylene-1,3-diazolidine-2,4-dione, and 2-[4-cyanomethyl-7-fluoro-2H-1,4-benzoxazin-3(4H)-on-6-yl]-hexahydro-1H-(1,2,4)-triazolo(1,2-a)pyridazine-1,3-dione.

If, for example, in the above process (a), 2-[7-fluoro-2H-1,4-benzoxazin-3(4H)-on-6-yl]-4,5,6,7-tetrahydro-2H-isoindole-1,3-dione and chloroacetonitrile are used as starting materials, the course of the reaction can be represented by the following equation:

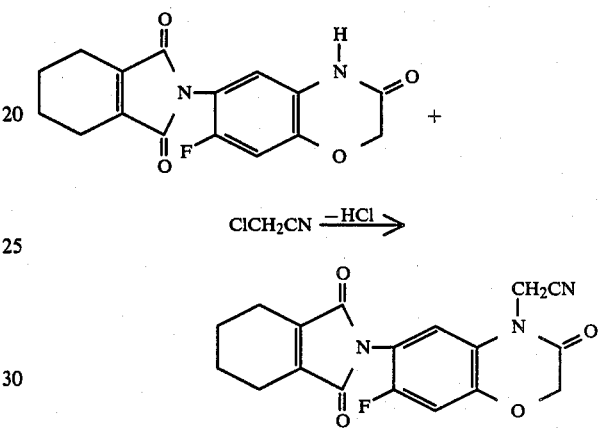

If, for example in the above process (b), 6-amino-4-(1-cyanoethyl)-2H-1,4-benzoxazin-3(4H)-one and tetrahydrophthalic anhydride are used as starting materials, the course of the reaction can be represented by the following equation:

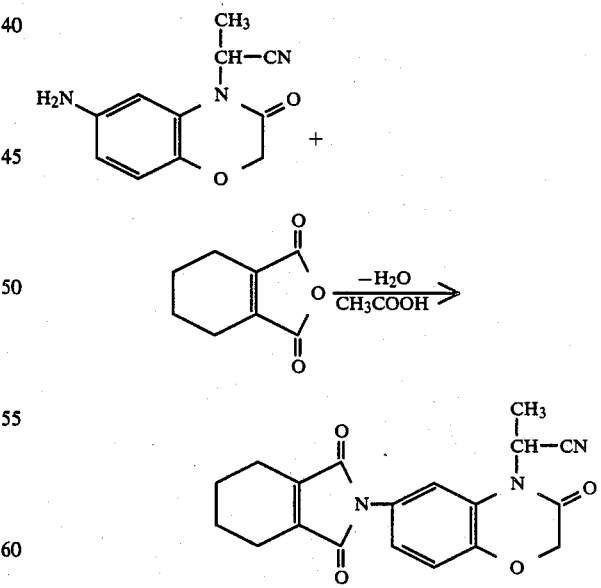

If, for example in the above process (c), 4-cyanomethyl-6-isocyanato-7-fluoro-2H-1,4-benzoxazin-3(4H)-one and 1-ethoxycarbonyl-hexahydropyridazine are used as starting materials, and then said product is cyclized, the course of the reaction can be represented by the following equation:

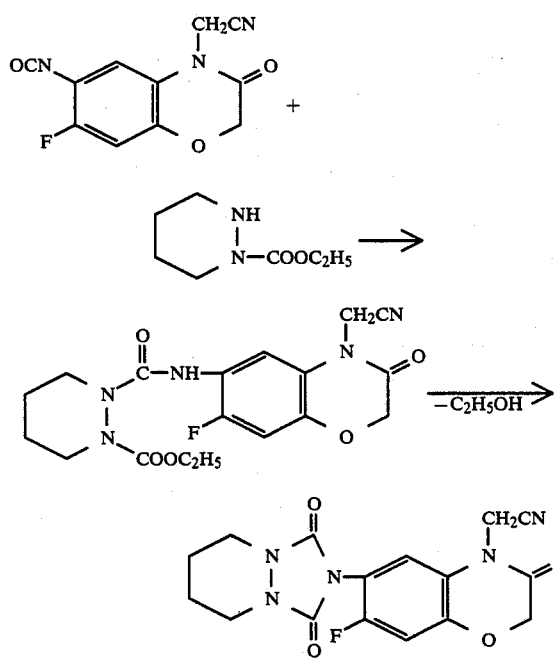

The compounds of the formula (II) are already known and in general can be obtained in accordance with a process described in Agr. Biol. Chem., Vol. 40, pp. 745 to 751, 1976 or Pestic. Biochem. Physiol., Vol. 14, pp. 153 to 160, as shown below.

In the case where Q is the group

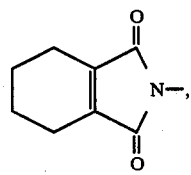

the compounds of the formula (II) can be obtained when compounds of the formula (VIII)

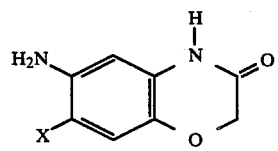
(VII)

wherein X has the same meanings as stated above, are reacted with tetrahydrophthalic anhydride in acetic acid under reflux.

The above formula (VII) can be obtained in general when compounds of the formula (VIII)

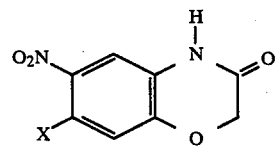
(VIII)

wherein X has the same meanings as stated above, are reduced, in which for instance, in the case where X is hydrogen, then the formula (VII) can be obtained when 6-nitro-1,4-benzoxazin-3(4H)-one is reduced, and 6-nitro-1,4-benzoxazin-3-4H)-one can be obtained when a known 2-hydroxy-5-nitroaniline is reacted with chloroacetylchloride, in accordance with a process described in Synthesis, 1984, p. 851 or Japanese Patent Laid-open No. 125,529/1974, and in the case where X is fluorine, then the formula (VII) can be obtained when 7-fluoro-6-nitro-1,4-benzoxazin-3(4H)-one is reduced, as above mentioned, and 7-fluoro-6-nitro-1,4-benzoxazin-3(4H)-one can be obtained when 7-fluoro-1,4-benzoxazin-3(4H)-one is nitrated, in accordance with a process described in Synthesis Organic Chemistry, R. B. Wagner and H. D. Zook, published by John Wiley & Sons Inc., 1953, p. 746, and 7-fluoro-1,4-benzoxazin-3(4H)-one can be obtained when 4-fluoro-2-hydroxyaniline is reacted with chloroacetylchloride, and 4-fluoro-2-hydroxyaniline can be obtained when a known 5-fluoro-2-nitrophenol is reduced, as above mentioned.

In the case where Q is

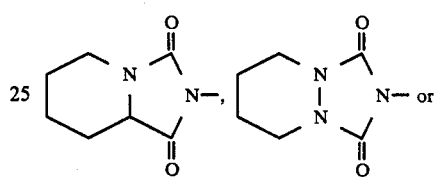

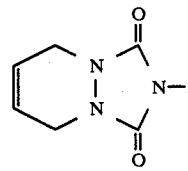

the compounds of the formula (II) can be obtained when compounds of the formula (IX)

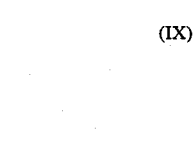
(IX)

wherein X has the same meanings as stated above, are reacted with the aforementioned compounds of the formula (VI), and then said products are cyclized in the presence of a base.

The compounds of the formula (IX) can be obtained when the aforementioned compounds of the formula (VII) ar reacted with phosgene or trichloromethyl chloroformate.

As examples of the compounds of the formula (II), there may be mentioned:

2-[7-fluoro-2H-1,4-benzoxazin-3(4H)-on-6-yl]-4,5,6,7-tetrahydro-2H-isoindole-1,3-dione, 2-[7-fluoro-2H-1,4-benzoxazin-3(4H)-on-6-yl]-hexahydro-1H-(1,2,4)-triazolo(1,2-a)pyridazine-1,3-dione, and 2-[7-fluoro-2H-1,4-benzoxazin-3(4H)-onn-6yl]-5,6,7,8-tetrahydroimidazo(1,5-a)pyridine-1,3-(2H,8aH)-dione.

In the formula (III), $R^1$ and $R^2$ preferably have the meanings already given above, and $M^1$ preferably represents chlorine or bromine.

The compounds of the formula (III) are already known. As examples there may be mentioned:
chloroacetonitrile,
trimethylsilylmethyl bromacetate, and
trimethylsilylmethyl chloroacetate.

For instance, trimethylsilylmethyl bromacetate can be obtained when trimethylsilylmethanol is reacted with bromacetylchloride or bromoacetylbromide in the presence of a base such as triethylamine.

The compounds of the formula (IV) are novel and can be easily obtained when compounds of the formula (X)

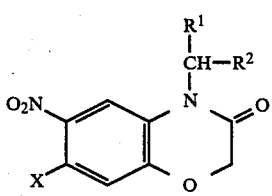  (X)

wherein X, $R^1$ and $R^2$ have the same meanings as stated above, are reduced, in accordance with a process described in J. Am. Chem. Soc., Vol. 77, p. 6266.

The compounds of the formula (X) are also novel and can be obtained when compounds of the formula (XI)

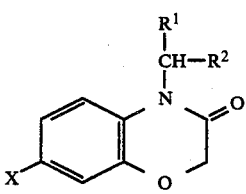  (XI)

wherein, X, $R^1$ and $R^2$ have the same meanings as stated above, are nitrated, or the aforementioned compounds of the formula (III) are reacted with the aforementioned compounds of the formula (VIII).

The compounds of the formula (XI) are also novel and can be obtained when compounds of the formula (XII)

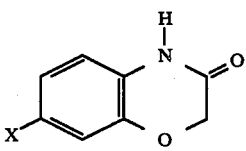  (XII)

wherein X has the same meanings as stated above, are reacted with the aforementioned compounds of the formula (III).

The compounds of the formula (XIII) can be obtained when compounds of the formula (XIII)

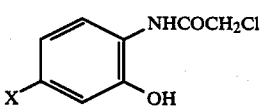  (XIII)

wherein X has the same meanings as stated above, are cyclized in the presence of a base.

The compounds of the formula (XIII) can be obtained when compounds of the formula (XIV)

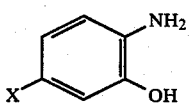  (XIV)

wherein X has the same meanings as stated above, are reacted with chloroacetylchloride, in accordance with a conventional method.

The formula (XIV), in the case where X is fluorine, corresponds to 4-fluoro-2-hydroxyaniline hereinafter and the formula (XIV), in the case where X is chlorine, can be obtained when known 6-chloro-2(3H)-benzoxazolone is hydrolyzed, in accordance with a process described in J. Am. Chem. Soc., Vol. 71, pp. 1265–1268.

In the case where $R^2$ is alkylthio, and $R^2$ becomes $R^3$, the compounds of the formula (X) can be obtained when compounds of the formula (XV)

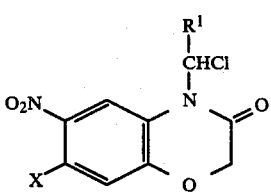  (XV)

wherein X and $R^1$ have the same meanings as stated above, are reacted with compounds of the formula (XVI)

 $R^3$—$M^2$  (XVI)

wherein
$R^3$ is $C_{1-4}$ alkylthio and
$M^2$ is alkali metal.

The compounds of the formula (XV) can be obtained when the aforementioned compounds of the formula (VIII) are reacted with aldehydes of the formula (XVII)

 $R^1$—CHO  (XVII)

wherein
$R^1$ has the same meaning as stated above, to form the compounds of the formula (XVIII)

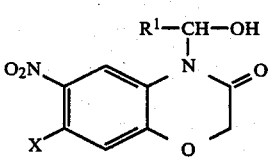  (XVIII)

wherein X and $R^1$ have the same meanings as stated above, and then said products are reacted with thionyl chloride.

The compounds of the formula (V) can be obtained when the aforementioned compounds of the formula (IV) are reacted with trichloromethyl chloroformate or phosgene.

The compounds of the formula (VI), in the case where W is the group

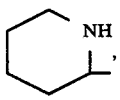

corresponds to pipecolinic acid or the ethyl ester thereof which are commercially available, and in the case where W is the group

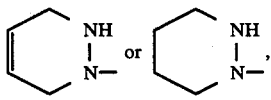

the aimed compounds corresponding to the formula (VI), respectively 1-ethoxycarbonyl-1,2,3,6-tetrahydropyridazine or 1-ethoxycarbonylhexahydropyridazine, can be obtained by way of 1,2-bis(ethoxycarbonyl-1,2,3,6-tetrahydropyridazine produced by reacting 1,3-butadiene and diethyl azodicarboxylate as starting materials. The compounds of the formula (IV), (X), (XI), (XV) and (XVIII) are new and may be summarized in the following formula (XIX)

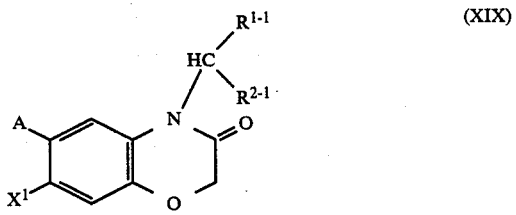

wherein
$R^{1-1}$ is hydrogen, methyl or ethyl,
$R^{2-1}$ is cyano, hydroxy, chlorine, trimethylsilyl, trimethylsilylmethoxycarbonyl, $C_1$–$C_4$-alkykthio or cyclopropyl,
A is hydrogen, amino or nitro and
$X^1$ is hydrogen or halogen,
with the proviso that A is nitro when $R^{2-1}$ is chlorine or hydroxy.

Preferred compounds of the formula (XIX) are those in which
$R^{1-1}$ is hydrogen or methyl,
$R^{2-1}$ is cyano, hydroxy, chlorine or $C_1$–$C_4$-alkylthio,
A is hydrogen, amino or nitro and
$X^1$ is hydrogen, fluorine or chlorine,
with the proviso that A is nitro when $R^{2-1}$ is chlorine or hydroxy. Particularly preferred compounds of the formula (XIX) are those, in which
$R^{1-1}$ is hydrogen or methyl,
$R^{2-1}$ is cyano, hydroxy, chlorine or methylthio,
A is hydrogen or nitro and
$X^1$ is hydrogen or fluorine,
with the priviso that A is nitro when $R^{2-1}$ is chlorine or hydroxy.

Suitable diluents in the process (a) are all inert organic solvents.

As examples, these preferentially include water, nitriles such as acetonitrile, alcohols such as ethanol, acid amides such as dimethylformamide, sulfoxides such as dimethylsulfoxide, ketones such as acetone, and the like.

The process (a) can also be carried out in the presence of a base.

As examples of bases, these preferentially include sodium carbonate, sodium hydride, potassium carbonate, potassium hydroxide, sodium hydroxide, sodium methoxide, sodium ethoxide, potassium tert-butoxide, and the like.

The reaction temperatures of the process (a) can be varied within a substantial range. In general, the reaction is carried out at between about 20 and about 150° C., preferably between about 30 and about 100° C.

The reaction of the process (a) can be carried out under normal, elevated or reduced pressure.

In carrying out the process (a), for example, about 1 to 1.2 moles of the compounds of the formula (III) may be employed per mole of the compounds of the formula (II), and these compounds are reacted in the presence of an inert solvent and in the presence of a base, so that the aimed compounds of the formula (I) can be obtained.

In carrying the process (b), suitable diluents include the same solvents as exemplified for the process (a).

The reaction temperatures of the process (b) can be varied within a substantial range. In general, the reaction is carried out at between about 70 and 280° C., preferably between about 80 and about 140° C.

The reaction of the process (b) can be carried out under normal, elevated or reduced pressure.

In carrying out the process (b), for example, about 1 to 1.2 moles of tetrahydrophthalic anhydride may be employed per mole of the compounds of the formula (IV), and these compounds are reacted in the presence of acetic acid, so that the aimed compounds of the formula (I) can be obtained.

In carrying out the process (c), suitable diluents include the same solvents as exemplified for the process (a).

The reaction temperatures of the process (c) can be varied within a substantial range. In general, the reaction is carried out at between about $-10$ and about 100° C., preferably between about 10 and about 100° C.

The reaction of the process (c) can be carried out under normal, elevated or reduced pressure.

In carrying out the process (c), for example, about 1 to 1.2 moles of the compounds of the formula (VI) may be employed per mole of the compounds of the formula (V), and these compounds are reacted in the presence of an inert solvent and then said products are cyclized in the presence of a base, so that the aimed compounds of the formula (I) can be obtained.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, suspensions, powders, foams, pastes, granules, aerosols, natural and synthetic materials impregnated with active compounds, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used nonionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between about 0.0005 and about 3 kg of active compound per hectare of soil surface, preferably between about 0.001 and about 2 kg per ha.

The preparation and the use of the active compounds according to the invention are illustrated by the following examples. It should be noted that the scope of the invention is not limited only to the technical contents of the examples.

PREPARATIVE EXAMPLES

EXAMPLE 1

(Compound No. 1)

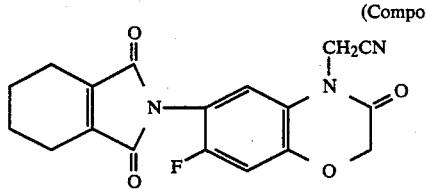

A suspension of 2-[7-fluoro-2H-1,4-benzoxazin-3(4H)-on-6-yl]-4,5,6,7-tetrahydro-2H-isoindole-1,3-dione (2 g) and potassium carbonate (1.05 g) in acetonitrile (30 ml) is refluxed for 30 minutes. The resulting solution is cooled to a temperature of 5° C. To the solution is added dropwise chloroacetonitrile (0.72 g), and thereafter the solution is refluxed for 3 hours. The solvent is distilled off, and the residue is admixed with water and subjected to an extraction operation with the aid of dichloromethane. The dichloromethane layer is separated off, washed with water, and dried over sodium sulfate. The solution is concentrated to precipitate a crystalline product, which is then recrystallized in a solvent consisting of acetonitrile and water. As an end product, 2-[7-fluoro-4-cyanomethyl-2H-1,4-benzoxazin-3(4H)-on-6-yl]-4,5,6,7-tetrahydro-2H-isoindole-1,3-dione (0.84 g) is obtained. mp. 216°-220° C.

EXAMPLE 2

(Compound No. 2)

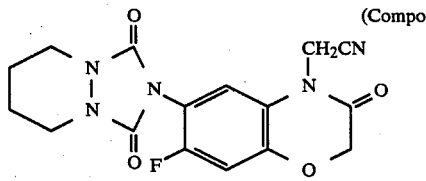

A mixture composed of 2-[7-fluoro-2H-1,4-benzoxazin-3(4H)-on-6-yl]-hexahydro-1H-(1,2,4)-triazolo (1,2-a)-pyridazine-1,3-dione (2.04 g), potassium carbonate (1.06 g), chloroacetonitrile (0.96 g) and acetonitrile (30 ml) is refluxed for 3 hours. The reaction mixture is made free from acetonitrile by evaporation in vacuo and mixed with water. The resultant solid is collected by filtration and washed with a small amount of ethanol to obtain an end product 2-[4-cyanomethyl-7-fluoro-2H-1,4-benzoxazin-3(4H)-on-6-yl]-hexahydro-1H-(1,2,4)-triazolo (1,2-a)-pyridazine-1,3-dione (1.62 g), mp. 286°-287° C.

EXAMPLE 3

(Compound No. 3)

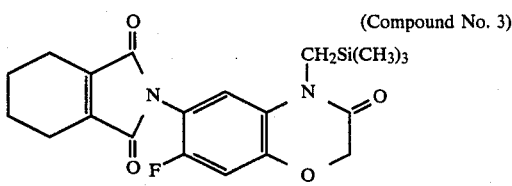

To N,N-dimethylformamide (10 ml) is added at an ambient temperature sodium hydride (0.1 g), sodium iodide (5 mg), 18-crown-6 (5 mg) and 2-[7-fluoro-2H-1,4-benzoxazin-3(4H)-on-6-yl]-4,5,6,7-tetrahydro-2H-isoindole-1,3-dione (0.63 g). Thereafter the whole is stirred for 15 minutes, treated with a solution of chloromethyltrimethylsilane (0.61 g) in N,N-dimethylformamide (5 ml), and stirred at 100°-110° C. for an hour. The reaction mixture is evaporated to dryness in vacuo, admixed with water (30 ml), and extracted twice with dichloromethane (30 ml). The combined extract is dried over sodium sulfate and evaporated in vacuo to obtain an oily end product 2-[7-fluoro-4-trimethylsilylmethyl-2H-1,4-benzoxazin-3(4H)-on-6-yl]-4,5,6,7-tetrahydro-2H-isoindole-1,3-dione (0.7 g). $n_D^{20}$ 1.5596.

The compounds of the formula (I), according to the invention which can be produced in the same manner as in Examples 1 to 3 in the following Table 1.

TABLE 1

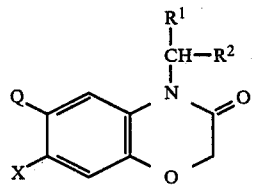

| Compd. No. | Q | X | $R^1$ | $R^2$ | |
|---|---|---|---|---|---|
| 4 | (4,5,6,7-tetrahydroisoindole-1,3-dione-2-yl) | H | $CH_3$ | —CN | mp. 189~190° C. |
| 5 | (4,5,6,7-tetrahydroisoindole-1,3-dione-2-yl) | F | $CH_3$ | —CN | mp. 159~160.5° C. |

TABLE 1-continued
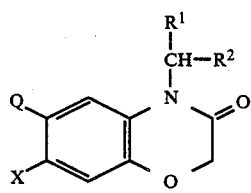
| Compd. No. | Q | X | R¹ | R² | |
|---|---|---|---|---|---|
| 6 | ![cyclohexene-dicarboximide] | F | H | —SCH₃ | |
| 7 | ![cyclohexene-dicarboximide] | F | H | —SC₂H₅ | |
| 8 | ![cyclohexene-dicarboximide] | H | H | —Si(CH₃)₃ | Viscous oil |
| 9 | ![hexahydroimidazopyridine-dione] | H | H | —CN | mp. 209~213° C. |
| 10 | ![hexahydroimidazopyridine-dione] | F | H | —CN | mp. 269~271° C. |
| 11 | ![tetrahydrotriazine-dione] | H | H | —CN | mp. 247~249° C. |
| 12 | ![dihydrotriazine-dione] | H | H | —CN | mp. 268~272° C. |

TABLE 1-continued

[Structure: benzoxazinone with Q and X substituents on benzene ring, and N-CH(R¹)-R² group]

| Compd. No. | Q | X | R¹ | R² | |
|---|---|---|---|---|---|
| 13 | [cyclic: hexahydro-1,2,4-triazolo-pyridazine-1,3-dione with double bond, attached via N] | F | H | —CN | mp. 233~237° C. |
| 14 | [hexahydrophthalimide-N—] | F | H | [cyclopropyl] | mp. 133~134° C. |
| 15 | [hexahydrophthalimide-N—] | H | H | —CN | mp. 180~182° C. |
| 16 | [hexahydrophthalimide-N—] | H | H | —COCH₂Si(CH₃)₃ | $n_D^{50}$ 1.5516 |
| 17 | [hexahydrophthalimide-N—] | F | H | —COCH₂Si(CH₃)₃ | $n_D^{20}$ 1.5446 |

EXAMPLE 4
(production of an intermediate)

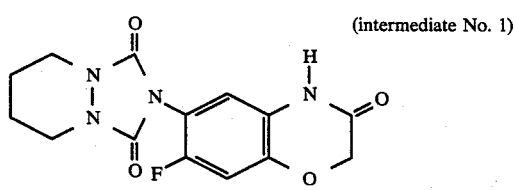

(intermediate No. 1)

A mixture composed of 6-isocyanato-7-fluoro-2H-1,4-benzoxazin-3(4H)-one (2.14 g), 1-ethoxycarbonylhexahydropyridazine (1.62 g) and dioxane (30 ml) is treated with a few drops of triethylamine, stirred at an ambient temperature for 2 hours, and left overnight. The reaction mixture is made free from dioxane by evaporation in vacuo, mixed with methanol (30 ml) containing a catalytic amount of sodium, and refluxed for 2 hours. After removal of methanol by evaporation in vacuo, the resultant solid is collected, and washed with water to obtain an end product 2-[7-fluoro-2H-1,4-benzoxazin-3(4H)-on-6-yl]-hexahydro-1H-(1,2,4)-triazolo (1,2-a) pyridazine-1,3-dione (2.45 g).

mp. 287°–290° C.

The reactant 6-isocyanato-7-fluoro-2H-1,4-benzoxazin-3(4H)-one is obtained by refluxing 6-amino-7-fluoro-2H-1,4-benzoxazin-3(4H)-one with an equimolar amount or a slight excess molar amount of trichloromethyl chloroformate in the presence of dioxane for a period necessary to make the refluxing mixture a clear solution, which can be used directly in further reaction without isolation or identification after removal of highly volatile substances by evaporation in vacuo.

EXAMPLE 5

(production of an intermediate)

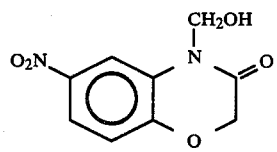 (intermediate No. 2)

A stirred mixture composed of 6-nitro-2H-1,4-benzoxazin-3(4H)-one (5.82 g), 37% formaldehyde aqueous solution (28.5 ml) and water (5.4 ml) is refluxed for 2 hours, and cooled. The resultant solid is collected by filtration, washed with water, ethanol, ether and n-hexane successively, and dried to obtain 4-hydroxymethyl-6-nitro-2H-1,4-benzoxazin-3(4H)-one (5.19 g).

mp. 239° C.

The following compound is also obtained by similar procedure:

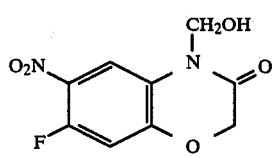 (intermediate No. 3)

EXAMPLE 6

(production of an intermediate)

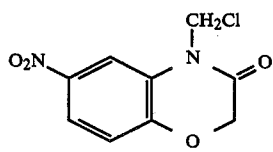 (intermediate No. 4)

To a suspension of 4-hydroxymethyl-6-nitro-2H-1,4-benzoxazin-3(4H)-one (22.42 g) in chloroform (50 ml) is added a catalytic amount of triethylamine. The mixture is stirred at ambient temperature, treated dropwise with thionyl chloride, and stirred at 60° C. for 6 hours. The reaction mixture is made free form insoluble materials by filtration and the filtrate is poured into water. The separated chloroform layer is washed with water, saturated sodium bicarbonate solution and saturated sodium chloride solution successively, dried, and evaporated to obtain 4-chloromethyl-6-nitro-2H-1,4-benzoxazin-3(4H)-one (17.23 g).

mp. 133° C.

The following compound is also obtained by similar procedure:

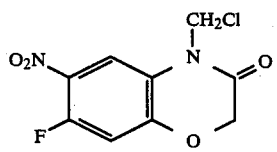 (intermediate No. 5)

EXAMPLE 7

(production of an intermediate)

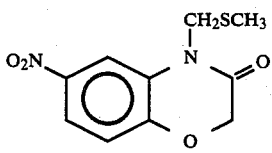 (intermediate No. 6)

Methyl mercaptan (1.9 g) is slowly introduced to a refluxing mixture composed of 4-chloromethyl-6-nitro-2H-1,4-benzoxazin-3(4H)-one (4.48 g), potassium carbonate (3.3 g) and methyl ethyl ketone (30 ml). The reaction mixture is refluxed for 5 hours, made free from methyl ethyl ketone by evaporation in vacuo, and the resultant residue is extracted with ethyl acetate. The extract is washed with saturated sodium carbonate aqueous solution and with water, dried over sodium sulfate, and condensed to ensure crystallization. The collected solid is washed with a small amount of ether to obtain 4-methylthiomethyl-6-nitro-2H-1,4-benzoxazin-3(4H)-one (2.3 g).

mp. 147° C.

EXAMPLE 8

(production of an intermediate)

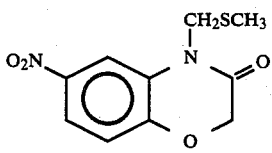 (intermediate No. 7)

Fuming (α 1.52) nitric acid (1.3 ml) is added dropwise to 0° C. to acetic anhydride (11.3 g), and thereafter a catalytic amount of concentrated sulfuric acid is added. To the solution is added portionwise at 0° C. 4-cyanomethyl-2H-1,4-benzoxazin-3(4H)-one (1.88 g). The mixture is stirred at 0° C. for 20 minutes, treated dropwise with a cold solution which is made by dissolving sodium hydroxide (10 g) in water (87.5 ml) and cooled to 0° C., stirred at 0° C. for 30 minutes to finish the reaction, and extracted with methyl isobutyl kotone. The extract is washed with water, dried, and evaporated. The resultant solid is recrystallized from ethanol to obtain an end product 4-cyanomethyl-6-nitro-2H-1,4-benzoxazin-3(4H)-one (1.3 g). mp. 173° C.

EXAMPLE 9

(production of an intermediate)

(intermediate No. 8)

A mixture of ethanol (15 ml), acetic acid (1 g), water (25 ml) and iron (3 g) is stirred at 80° C., and 4-cyanomethyl-6-nitro-2H-1,4-benzoxazin-3(4H)-one (2.33 g) is added portionwise thereto. The whole is stirred at 80° C. until gas evolution ceases. The reaction mixture is mixed with active carbon (1 g) and ethanol (20 ml), refluxed for 15 minutes, and filtered. The filtrate is poured into chilled water. The deposited crystals are collected by filtration, and dried to obtain 6-amino-4-cyanomethyl-2H-1,4-benzoxazin-3(4H)-one (1.51 g).

mp. 158° C.

Intermediates which can be produced in the same manner as in Example 5–9 are shown in the following Table 2.

TABLE 2

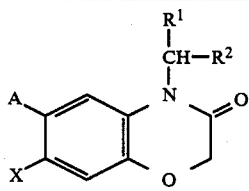

| Intermediate No. | A | X | $R^1$ | $R^2$ | |
|---|---|---|---|---|---|
| 9 | H | H | H | CN | mp. 115° C. |
| 10 | H | F | H | CN | mp. 111° C. |
| 11 | H | Cl | H | CN | mp. 132° C. |
| 12 | $O_2N$ | F | H | CN | mp. 205° C. |
| 13 | $O_2N$ | F | $CH_3$ | CN | |
| 14 | $O_2N$ | Cl | H | CN | mp. 187° C. |
| 15 | $O_2N$ | H | H | $SC_2H_5$ | |
| 16 | $H_2N$ | F | H | CN | mp. 167° C. |
| 17 | $H_2N$ | Cl | H | CN | mp. 180° C. |
| 18 | $H_2N$ | H | $CH_3$ | CN | |
| 19 | $H_2N$ | F | $CH_3$ | CN | |
| 20 | $H_2N$ | H | H | $SCH_3$ | |
| 21 | $H_2N$ | H | H | $SC_2H_5$ | |
| 22 | $H_2N$ | F | H | $SCH_3$ | |
| 23 | $H_2N$ | F | H | $SC_2H_5$ | |

BIOLOGICAL TESTS

Comparative compound (E-1)

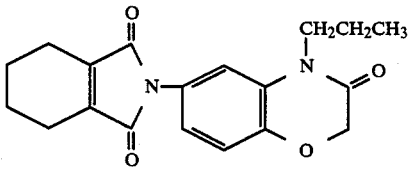

(the compound described in Japanese Laid-Open Patent Publication No. 30586/1986)

Example 10

Test on weeds in a flooded paddy by water surface application:
Preparation of an active compound formulation
Carrier: 5 parts by weight of acetone
Emulsifier: 1 part by weight of benzyloxy polyglycol ether A formulation of an active compound was otained as an emulsifiable concentrate by mixing 1 part by weight of the active compound with the above-mentioned amounts of the carrier and the emulsifying agent. A predetermined amount of the formulation was diluted with water.

Testing method

Paddy soil was filled in pots (1/2,000 are; 25×20×9 cm), and rice seedlings (variety: "Nihonbare") in the 2.5-leaf stage (15 cm tall) were transplanted at two places per pot each as a stock of three seedlings. Seeds of barnyard grass (Echinochloa oryzicola Vasing.), umbrella plant (Cyperus difformis L.), monochoria (Monochoria vaginalis), and annual broadleaved weeds false pimpernel (Lindernia pyxidaria L.), Rotala indica, American waterwort (Elatine triandra), red stem (Ammannia multiflora Roxburgh) and Dopatrium junceum Hamilton were sown and the pots were maintained wet. Two days later, the pots were flooded to a depth of about 2 to 3 cm. Five days after the transplantation of the seedlings, the compound of this invention, in the form of an emulsifiable concentrate as prepared above, was applied to the water surface by a pippette in a predetermined amount. Thereafter, the flooded condition of about 3 cm was maintained, and four weeks after the chemical treatment, the herbicidal effect and the phytotoxicity to rice were evaluated and rated on the scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to crop (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 3 by typical examples.

TABLE 3

| Compounds No. | Amount of the active ingredient (kg/ha) | Herbicidal effect | | | Phytotoxicity Rice |
|---|---|---|---|---|---|
| | | Barnyard grass | Umbrella plant | Monochoria | Broadleaved weeds | |
| 5 | 0.25 | 5 | 5 | 5 | 5 | 2 |
| | 0.125 | 4 | 5 | 5 | 5 | 1 |
| | 0.06 | 4 | 5 | 5 | 5 | 0 |
| 15 | 0.25 | 5 | 5 | 5 | 5 | 2 |
| | 0.125 | 4 | 5 | 5 | 5 | 1 |
| | 0.06 | 4 | 5 | 5 | 5 | 0 |
| Comparison E-1 | 0.5 | 5 | 5 | 5 | 5 | 4 |
| | 0.25 | 3 | 5 | 4 | 4 | 3 |
| | 0.125 | 1 | 4 | 2 | 2 | 2 |

EXAMPLE 11

Test on upland weeds by soil treatment before emergence:

In a greenhouse, soybean seeds were sown in 500 cm² pots filled wth upland farm soil, and soil containing seeds of barnyard grass (Echinochloa crus-galli), lived amaranth (Amaranthus lividus L.) and goosefoot (Chenopodium album L.) was put over the soil in the pots in a depth of 1 cm.

One day after the sowing, a test chemical in a predetermined concentration, prepared as in Example 10, was uniformly sprayed over the surface layer of the soil in each of the test pots.

Four weeks after the spraying, the herbicidal effect and the phytotoxicity to crops were examined on the same standards as in Example 10. The results are shown in Table 4 by typical examples.

TABLE 4

| Compound No. | Amount of the active ingredient (kg/ha) | Herbicidal effect | | | Phyto-toxicity Soybean |
|---|---|---|---|---|---|
| | | Barn-yard grass | Livid amaranth | Goose-foot | |
| 1 | 0.25 | 5 | 5 | 5 | 1 |
| | 0.125 | 4 | 5 | 5 | 0 |
| | 0.06 | 3 | 5 | 5 | 0 |
| 5 | 0.25 | 5 | 5 | 5 | 1 |
| | 0.125 | 4 | 5 | 5 | 0 |
| | 0.06 | 3 | 5 | 5 | 0 |
| Comparison E-1 | 0.5 | 4 | 5 | 5 | 4 |
| | 0.25 | 3 | 5 | 5 | 3 |
| | 0.125 | 3 | 4 | 3 | 3 |

EXAMPLE 12

Test on upland farm weeds by foliar treatment

In a greenhouse, wheat seeds were sown in 500 cm² pots filled with upland farm soil, and soil containing seeds of Digitaria (*Digitaria sanguinalis*), lived amaranth (*Amaranthus lividus* L.) and goosefoot (*Chenopodium album* L.) was put over the soil in the pots in a depth of 1 cm.

After sowing, the plants were grown for 14 day and a test chemical in a predetermined concentration, prepared as in Example 10, was uniformly sprayed over the test plants in each of the test pots.

Four weeks after the spraying, the herbicidal effect and the phytotoxicity to crops were examined on the same standards as in Example 10. The results are shown in Table 5 by typical examples.

TABLE 5

| Compound No. | Amount of the active ingredient (kg/ha) | Herbicidal effect | | | Phyto-toxicity Wheat |
|---|---|---|---|---|---|
| | | Digi-taria | Livid amaranth | Goose-foot | |
| 2 | 0.25 | 5 | 5 | 5 | 1 |
| | 0.125 | 5 | 5 | 5 | 0 |
| | 0.06 | 4 | 5 | 5 | 0 |
| 10 | 0.5 | 5 | 5 | 5 | 1 |
| | 0.25 | 5 | 5 | 5 | 0 |
| | 0.125 | 4 | 5 | 5 | 0 |
| 16 | 1 | 5 | 5 | 5 | 1 |
| | 0.5 | 5 | 5 | 5 | 0 |
| | 0.25 | 4 | 5 | 5 | 0 |
| 17 | 0.5 | 5 | 5 | 5 | 1 |
| | 0.25 | 5 | 5 | 5 | 0 |
| | 0.125 | 4 | 5 | 5 | 0 |
| Comparison E-1 | 1 | 5 | 5 | 5 | 4 |
| | 0.5 | 5 | 5 | 5 | 3 |
| | 0.25 | 4 | 5 | 5 | 3 |

It will be appreciated that the instant specification and claims are set forth by way of illustration and not limitation, and that various modifications and changes may be made without departing from the spirit and scope of the present invention.

What is claimed is:

1. A benzoxazine of the formula

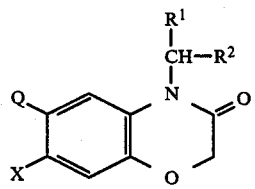

in which

X is hydrogen or halogen,
$R^1$ is hydrogen or $C_1$-$C_2$ alkyl,
$R^2$ is cyano, trimethylsilyl, trimethylsilylmethoxycarbonyl or cyclopropyl, and
Q is

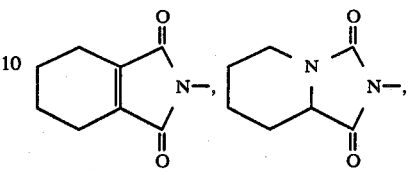

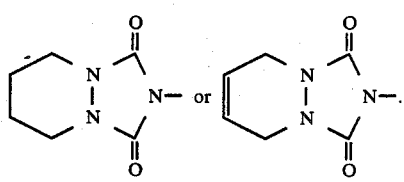

2. A compound according to claim 1, in which
X is hydrogen, fluorine or chlorine,
$R^1$ is hydrogen or methyl, and
$R^2$ is cyano, trimethylsilyl, trimethylsilylmethoxycarbonyl or cyclopropyl.

3. A compound according to claim 1, in which
X is hydrogen or fluorine,
$R^1$ is hydrogen or methyl, and
$R^2$ is cyano.

4. A compound according to claim 1, wherein such compound is
2-[4-cyanomethyl-7-fluoro-2H-1,4-benzoxazin-3(4H)-on-6-yl]-4,5,6,7-tetrahydro-2H-isoindole-1,3-dione of the formula

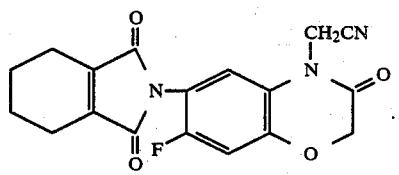

5. A compound according to claim 1, wherein such compound is
2-[4-(1-cyanoethyl)-7-fluoro-2H-1,4-benzoxazin-3(4H)-on-6-yl]-4,5,6,7-tetrahydro-2H-isoindole-1,3-dione of the formula

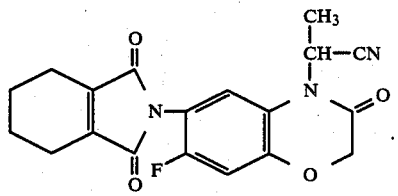

6. A compound according to claim 1, wherein such compound is
3-[4-cyanomethyl-7-fluoro-2H-1,4-benzoxazin-3(4H)-on-6-yl]-1,5-tetramethylene-1,3-diazolidine-2,4-dione of the formula

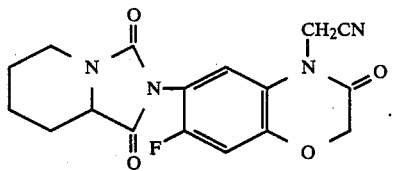

7. a compound according to claim 1, wherein such compound is
2-[4-cyanomethyl-7-fluoro-2H-1,4-benzoxazin-3(4H)-on-6-yl]-hexahydro-1H-(1,2,4)-triazolo (1,2-a)-pyridazine-1,3-dione of the formula

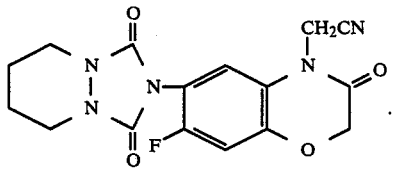

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
2-[4-cyanomethyl-7-fluoro-2H-1,4-benzoxazin-3(4H)-on-6-yl]-4,5,6,7-tetrahydro-2H-isoindole-1,3-dione;
2-[4-(1-cyanoethyl)-7-fluoro-2H-1,4-benzoxazin-3(4H)-on-6-yl]-4,5,6,7-tetrahydro-2H-isoindole-1,3-dione;
3-[4-cyanomethyl-7-fluoro-2H-1,4-benzoxazin-3(4H)-on-6-yl]-1,5-tetramethylene-1,3-diazolidine-2,4-dione;
2-[4-cyanomethyl-7-fluoro-2H-1,4-benzoxazin-3(4H)-on-6-yl]-hexahydro-1H-(1,2,4)-triazolo (1,2-a)-pyridazine-1,3-dione.

* * * * *

UNITED STATES PATENT AND TRADEMARK OFFICE
CERTIFICATE OF CORRECTION

PATENT NO. : 4,804,394

DATED : February 14, 1989

INVENTOR(S) : Toyohiko Kume, et al

It is certified that error appears in the above-identified patent and that said Letters Patent is hereby corrected as shown below:

| | |
|---|---|
| Col. 1, line 65 | Delete "$F^1$" and substitute --$R^1$-- |
| Col. 2, line 64 | Delete "(IV)" and substitute --(VI)-- |
| Col. 3, line 25 | After "cyclopropyl, and" insert --Q is-- |
| Col. 5, line 44 | Delete "(VIII)" and substitute --(VII)-- |
| Col. 6, line 54 | Delete "ar" and substitute --are-- |
| Col. 6, line 63 | Delete "-onn-" and substitute -- -on- -- |
| Col. 7, lines 4, 6 | Correct spelling of --bromoacetate-- |
| Col. 7, line 8 | Correct spelling of --bromoacetylchloride-- |
| Col. 7, line 56 | Before "can" delete "(XIII)" and substitute --(XII)-- |
| Col. 8, line 12 | Delete "hereinafter" and substitute --hereinbefore-- |
| Col. 9, line 59 | Delete "priviso" and substitute --proviso-- |

UNITED STATES PATENT AND TRADEMARK OFFICE
CERTIFICATE OF CORRECTION

PATENT NO. : 4,804,394

DATED : February 14, 1989

INVENTOR(S) : Toyohiko Kume, et al

It is certified that error appears in the above-identified patent and that said Letters Patent is hereby corrected as shown below:

Col. 22, line 56            Delete "wth" and substitute --with--

Signed and Sealed this

Twenty-third Day of January, 1990

Attest:

JEFFREY M. SAMUELS

*Attesting Officer*      *Acting Commissioner of Patents and Trademarks*